United States Patent
Bellows et al.

(10) Patent No.: US 11,191,608 B2
(45) Date of Patent: Dec. 7, 2021

(54) AERODYNAMICALLY SHAPED SURGICAL LIGHTING SUSPENSION

(71) Applicant: AMERICAN STERILIZER COMPANY, Mentor, OH (US)

(72) Inventors: Lance Clark Bellows, Leroy Township, OH (US); Damon Jurkiewicz, Cleveland, OH (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 571 days.

(21) Appl. No.: 15/914,512

(22) Filed: Mar. 7, 2018

(65) Prior Publication Data
US 2018/0256281 A1 Sep. 13, 2018

Related U.S. Application Data

(60) Provisional application No. 62/468,469, filed on Mar. 8, 2017.

(51) Int. Cl.
*A61B 90/50* (2016.01)
*A61B 90/35* (2016.01)

(52) U.S. Cl.
CPC .............. *A61B 90/35* (2016.02); *A61B 90/50* (2016.02)

(58) Field of Classification Search
CPC ......... A61B 90/30; A61B 90/35; A61B 90/50; A61B 2090/308
See application file for complete search history.

(56) References Cited

U.S. PATENT DOCUMENTS

| 6,203,175 | B1 | 3/2001 | Basacchi | |
|---|---|---|---|---|
| 2002/0064038 | A1 | 5/2002 | Kummerfeld | |
| 2006/0007691 | A1 | 1/2006 | Depenbusch et al. | |
| 2008/0192483 | A1* | 8/2008 | Mangiardi | A61B 90/35 362/319 |
| 2012/0267499 | A1* | 10/2012 | Abri | A61B 90/35 248/298.1 |
| 2015/0103527 | A1 | 4/2015 | Chang et al. | |
| 2015/0292720 | A1 | 10/2015 | Kelly | |
| 2015/0369455 | A1 | 12/2015 | Nieminen | |
| 2018/0245569 | A1* | 8/2018 | Lyatkher | F03D 3/062 |

OTHER PUBLICATIONS

International Search Report issued in corresponding PCT Application No. PCT/US2018/021342, dated May 10, 2018.
Extended European Search Report dated Nov. 25, 2020 from related/corresponding European Patent Appl. No. 18764679.9, filed Aug. 7, 2019.
Anonymous: Generating eco-friendly power with metal rotor blades:, May 7, 2015, URL: https://phys.org/news/2015-05-eco-friendly-power-metal-rotor-blades.html, retrieved on Nov. 17, 2020.
Anonymous: "Duckworks—Extruded Aluminum Hydrofoils", Mar. 21, 2015, URL: https://www.duckworksmagazine.com/15/howto/windknife/index.htm#, retrieved on Nov. 17, 2020.

* cited by examiner

*Primary Examiner* — Zade Coley
(74) *Attorney, Agent, or Firm* — Kusner & Jaffe

(57) ABSTRACT

A support arm for supporting a surgical device in an operating room. The support arm is comprised of an elongated, tubular extrusion having an inverted, generally tear-drop shaped outer surface that has an airfoil shape. The airfoil shape is symmetrical about an axis extending from a leading end of the airfoil to a trailing end of the airfoil shape.

13 Claims, 3 Drawing Sheets

AERODYNAMICALLY SHAPED SURGICAL LIGHTING SUSPENSION

FIELD OF THE INVENTION

The present invention relates to surgical lighting systems, and more particularly to an aerodynamically shaped surgical lighting system.

BACKGROUND OF THE INVENTION

With the advent of laminar air flow systems in modern operating rooms (ORs), a need has arisen to keep air flow turbulence in an operating room to a minimum to reduce the threat of illnesses due to airborne contaminants. A surgical light head, typically found in operating rooms over a surgical table, is a large contributor to air flow turbulence. In this respect, lighting suspension components, such as support arms and booms, contribute to air flow turbulence. Most currently available surgical lighting suspension systems have horizontal extension arms that have circular (including cylindrical), rectangular, or a combination of round and rectangular features.

The present invention provides a surgical lighting system with components shaped to reduce air flow turbulence in operating rooms (ORs) with laminar air flow systems.

SUMMARY OF THE INVENTION

In accordance with the present invention, there is provided a surgical lighting system having aerodynamically shaped components to reduce turbulence within operating rooms having laminar air flow systems.

In accordance with another aspect of the present invention, there is provided a support arm for supporting a surgical light head, comprised of an elongated, tubular extrusion having an inverted, generally tear-drop shaped outer surface that is symmetrical about a vertical axis. The outer surface is comprised of an arcuate top surface section having a surface radius $R_T$, an arcuate bottom surface section having a surface radius $R_B$, and opposing side surface sections. Each side surface section defines a section of an airfoil. The radius $R_B$ of the bottom surface section is less than half the radius $R_B$ of the top surface section, and the ends of the bottom surface sections intersect the ends of the side surface sections tangent to the ends of the side surface sections to form a continuous smooth profile.

In yet another aspect of the present invention, there is provided a support arm for supporting a surgical device in an operating room. The support arm is comprised of an elongated, tubular extrusion having an inverted, generally tear-drop shaped outer surface that has an airfoil shape. The airfoil shape is symmetrical about an axis extending from a leading end of the airfoil to a trailing end of the airfoil shape. The trailing edge of the airfoil shape has a round contour.

An advantage of the present invention is a surgical lighting system having a lower coefficient of drag in operating rooms equipped with laminar air flow systems.

Another advantage of the present invention is a surgical lighting system with reduced air flow turbulence in an operating room equipped with laminar air flow systems.

A still further advantage of the present invention is a surgical lighting system that reduces the threat of airborne illness in operating rooms equipped with laminar air flow systems by reducing turbulence of air flow around the lighting systems.

A still further advantage of the present invention is a surgical lighting system having components designed with aerodynamic shapes to reduce drag and turbulence in operating rooms equipped with laminar airflow system.

BRIEF DESCRIPTION OF THE DRAWINGS

The invention may take physical form in certain parts and in arrangement of parts, a preferred embodiment of which will be described in detail in the specification and illustrated in the accompanying drawings, which form a part thereof, and wherein.

DETAILED DESCRIPTION OF THE INVENTION

Figure 1:
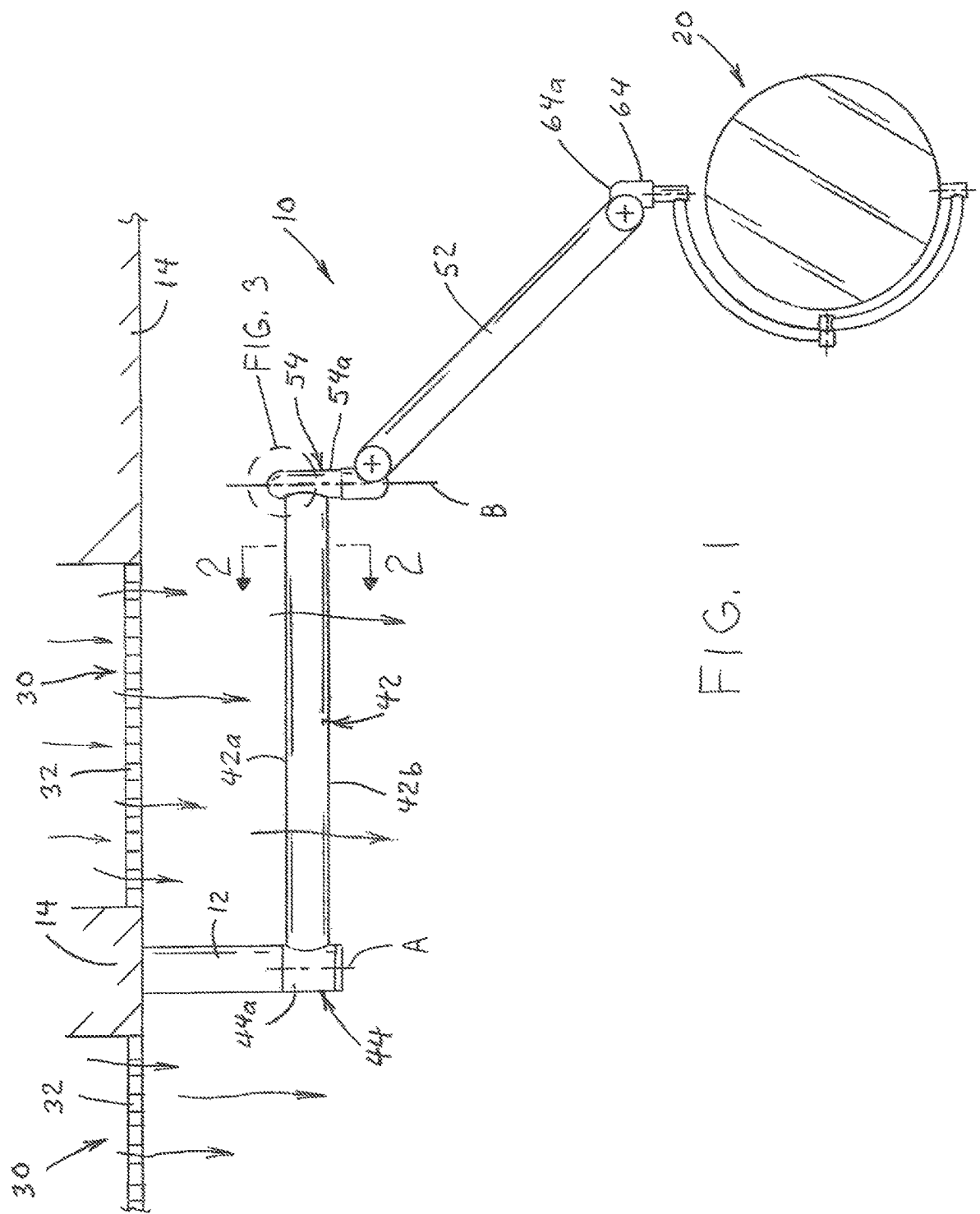
FIG. 1 is a view of surgical light system.

Referring now to the drawings wherein the showing is for the purpose of illustrating preferred embodiments of the invention only and not for the purpose of limiting same. FIG. 1 shows a support arm assembly 10 for supporting a surgical light fixture 20 in a surgical suite. Although light fixture 20 is shown, support arm assembly 10 may be used to support a monitor or a video camera or some other medical device (not shown).

Support arm assembly 10 is mounted by a central support 12 to a support member such a ceiling 14 or a wall mounted plate (not shown). Support arm assembly 10 is provided to allow light fixture 20 to be positioned for achieving a desired level of illumination on a subject below. In this respect, support arm assembly 10 and surgical tight 20 are typically positioned above a surgical table (not shown). Support arm assembly 10 is articulated to allow equipment, such as the light fixture, to be positioned relative to the surgical table.

FIG. 1 shows support arm assembly 10 mounted beneath a laminar air flow system 30 mounted within ceiling 14. Laminar air flow systems 30 are conventionally known and are provided for directing clean, filtered air downward over the surgical site, i.e., the surgical table. In the drawings, the components forming laminar air flow system 30 are not shown. Only vents 32 in ceiling 14 are illustrated with direction of air flow downward towards a surgical cite illustrated by downward directed arrows.

In the embodiment shown, support arm assembly 10 includes a proximal arm section 42 and a distal arm section 52. As illustrated in FIG. 1, proximal arm section 42 is positioned within the path of the air flow from laminar air flow system 30.

In the embodiment shown, support arm assembly 10 has two joints designated 44, 54. First joint 44 allows rotational movement of proximal arm section 42 about a vertical axis A extending through central support 12. Second joint 54 allows rotational movement of distal arm section 52 about an axis B relative to proximal arm section 42. Both joint assemblies 44, 54 are comprised of an outer housing 44a, 54a that covers the actual joint. As illustrated in FIG. 1, and best seen in 3, the upper end of housing 54a is contoured to produce more a uniform laminar flow over the joint. As partially seen in FIG. 1, the upper surface of a third joint 64a is also contoured to produce a more laminar flow.

Figure 2:
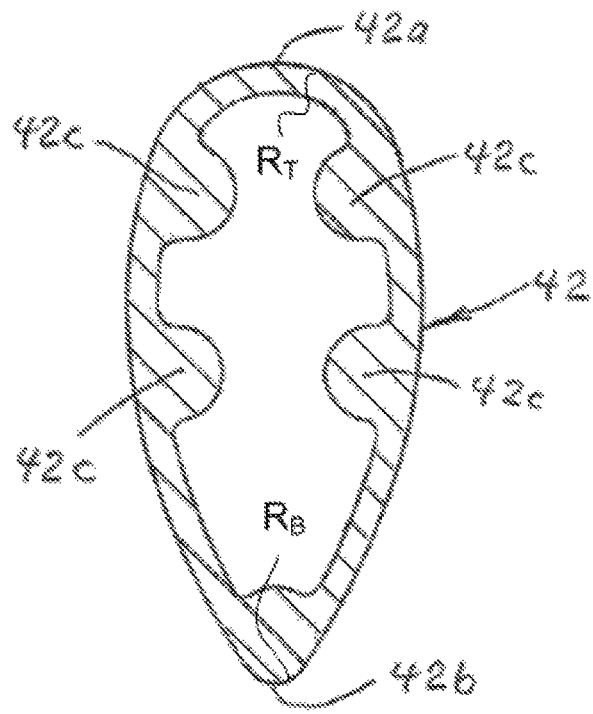
FIG. 2 is a sectional view taken along lines 2-2 of FIG. 1, showing the shape of a support arm.
Figure 3:
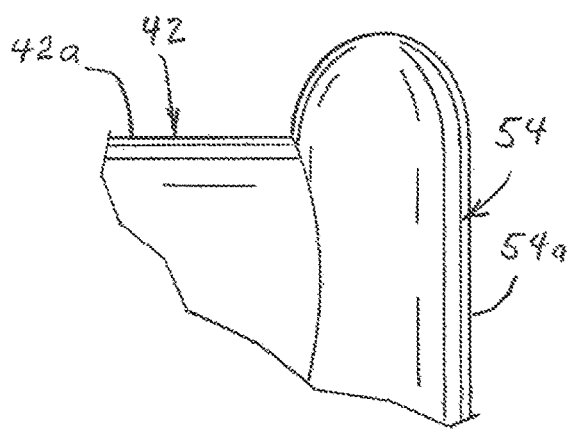
FIG. 3 is an enlarged view of a joint assembly shown in FIG. 1.

Referring now to FIG. 2, a cross-section of proximal arm section 42 is shown. Proximal arm section 42 is preferably formed of an extruded material having a uniform cross section along a length thereof. In the embodiment shown, the cross-sectional shape of proximal arm section 42 is substantially an airfoil having an upper leading edge 42a and a lower trailing edge 42b with respect to the direction of air flow from laminar air system 30. As used herein, "substantially" refers to the fact that proximal arm section 42 is not a true airfoil in the sense that the bottom or trailing edge 42b of proximal arm section 42 is rounded, as compared to a true airfoil where the trailing edge or bottom edge 42b would come to a point. In this respect, although not a true, exact airfoil, rounding of trailing edge 42b has little effect with respect to actual air flow flowing over proximal arm section 42 as compared to if proximal arm section 42 had a true airfoil shape. In other words, rounding trailing edge 42b produces little distortion in the air flow over proximal arm section 42 as compared to a cross-sectional shape having a pointed, trailing edge shape.

The cross section of proximal arm section 42 is symmetrical about an axis through the cross-section from leading edge 42a to trailing edge 42b. In other words, in the embodiment shown in FIG. 2, the right side of the cross-section is a mirror image of the cross-section. As shown in FIG. 2, inwardly projecting areas 42c extend along the length of proximal arm section 42. These areas 24c provide structural strength to proximal arm section 42, as well as surface areas at the ends of proximal arm section 42 for attachment to first joint 44 and second joint 54.

According to preferred embodiment of the present invention, the cross-sectional shape of proximal arm section 42 is based upon a standard set by the National Advisory Committee for Aeronautics (NACA). More specifically, proximal arm section 42 is based upon a NACA 0040 standard airfoil, which is a symmetrical airfoil with a maximum thickness of 40% of the cord length, i.e., the length from leading edge 42a to trailing edge 42b. Proximal arm section 42 is preferably formed of metal, and more preferably, is an aluminum extrusion.

Figure 5:
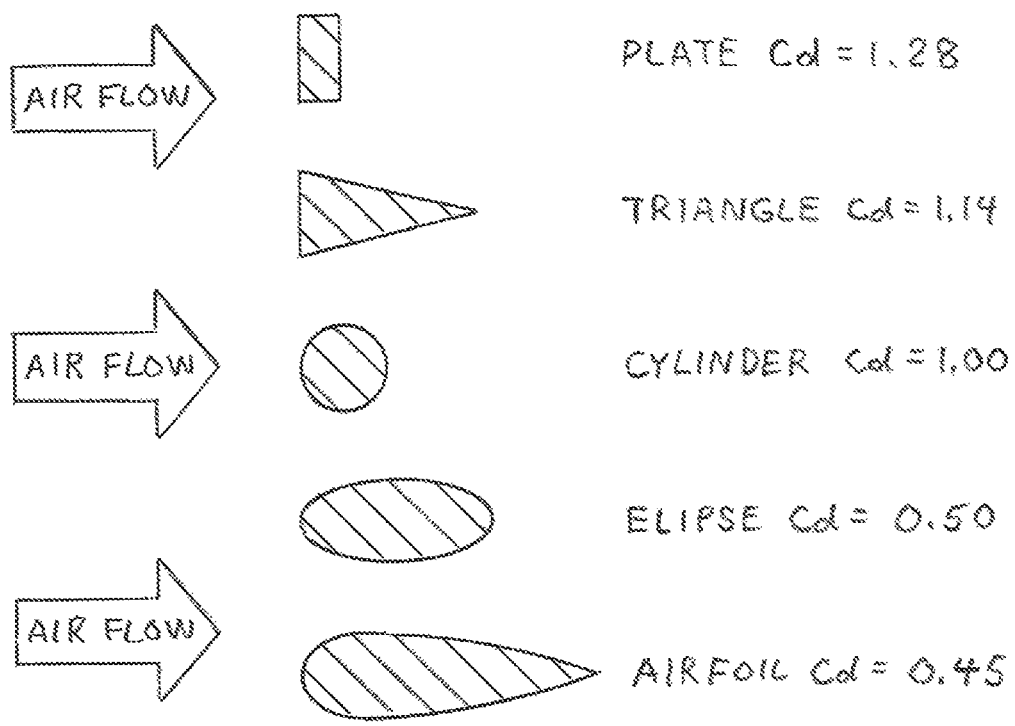
FIG. 5 is a table showing comparative drag coefficient for different cross-sectional shapes.

FIG. 5 shows a Table of drag co-efficient for a number of different cross-sectional shapes. As shown in the Table in FIG. 5, the drag coefficient of an airfoil is significantly less as compared to a conventional cylindrical shape or a rectangular shape. In this respect, providing proximal arm section 42 in the shape of an airfoil significantly reduces turbulence of the air flowing over support arm 10 from laminar air flow system 30 and is believed to reduce turbulence and distortion downstream of (i.e., below) proximal support arm section 42, i.e., in the vicinity of the surgical table.

In accordance with the present invention, the distal arm section 52 has a similar airfoil cross-section to reduce turbulent flow thereover.

Figure 4:
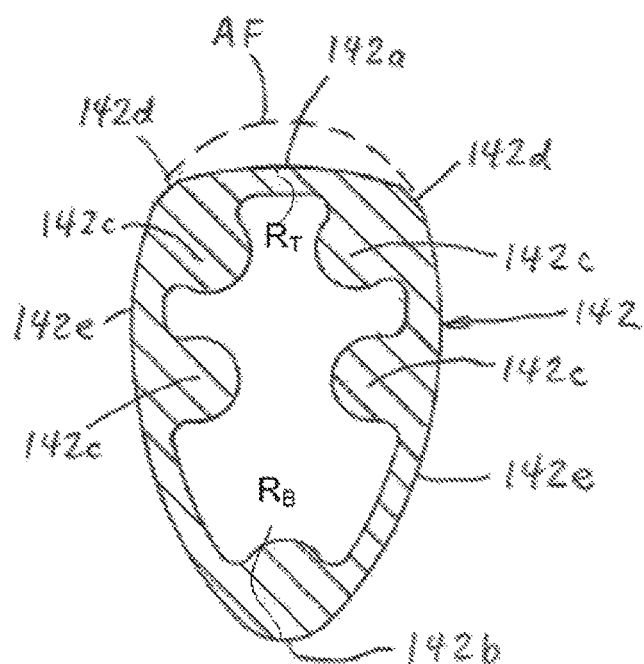
FIG. 4 is a cross sectional view of an alternate embodiment of a support arm.

Referring now to FIG. 4, a cross-sectional shape of a boom arm 142 illustrating an alternate embodiment of the invention is shown. In FIG. 4, a dotted line designated AF at the upper end of the cross-section illustrates the profile of a true airfoil. In this respect, the cross-section of boom arm 142 shown in FIG. 4, including the dotted line AF, would have an airfoil designated by NACA 0040 Standards. FIG. 4 shows a modification to a true airfoil where an upper leading edge 142a of boom arm 142 in the direction of air flow is modified and includes two flat surfaces 142d for aesthetic purposes. Even with such a modified airfoil shape, the side 142e and bottom or trailing edge 142b of boom arm 142 maintains an airfoil shape. It is believed that the shape shown in FIG. 4 would substantially reduce turbulent flow over boom arm 142. More specifically, leading edge 142a is an arcuate surface having a surface radius $R_L$. Boom arm 142 has an arcuate, bottom surface having a surface radius $R_B$. The ends of bottom surface $R_B$ intersect the ends of side surfaces 142e tangent to the ends of side surfaces 142e to form a continuous, smooth profile. Preferably, the radius $R_B$ of the bottom surface section is less than of half the radius $R_L$ of top leading surface 142a, The cross-sectional shape of boom arm 142 is based upon a NACA 0068 airfoil, wherein the airfoil has a width-to-cord length ratio of about 68%. More specifically, as indicated above, leading edge 142a is modified from a true airfoil AR In the embodiment shown, the cross-sectional shape of boom arm 142 has an overall length from leading edge 142a to bottom edge 142b of 85 mm and an overall maximum width of 55 mm. The radius of curvature of leading edge 142a is approximately 64 mm, and the radius of curvature of trailing edge 142b is 10 mm. Side surfaces 142e have the general shape of the NACA 0068 airfoil, as set forth above.

Boom arm 142 is preferably formed of an extruded metal, and more preferably is formed of aluminum.

Modifications and alterations of the structures shown in the drawings will become apparent to those skilled in the art after reading the present specification. It is intended that all such modifications and all variations being included in so far as they come within the scope of the patent as claimed or the equivalence thereof.

Having described the invention, the following is claimed:

1. A support arm for supporting a surgical light head, comprised of:
    an elongated, tubular extrusion having an inverted, generally tear-drop shaped cross-section, said cross-section having an outer surface that is symmetrical about a vertical axis, said outer surface comprised of
        an arcuate top surface section having a surface radius $R_T$,
        an arcuate bottom surface section having a surface radius $R_B$, and opposing side surface sections, each side surface section defining a section of an airfoil
    wherein said radius $R_B$ of said bottom surface section is less than half said radius $R_T$ of said top surface section, and
    wherein the ends of bottom surface section intersect the end of said side surface sections tangent to said ends of said side surface sections to form a continuous smooth profile.

2. A support arm for supporting a surgical light head according to claim 1, wherein said cross-section is based upon a NACA 0068 airfoil design.

3. A support arm for supporting a surgical light head according to claim 2, wherein said cross-section has a length from a top leading edge of said top arcuate surface to a bottom edge of said arcuate bottom surface of about 85 mm and a maximum width of about 55 mm.

4. A support arm for supporting a surgical light head according to claim 2, wherein said radius $R_T$ of said arcuate top surface is about 64.6 mm.

5. A support arm for supporting a surgical light head according to claim 4, wherein said radius $R_B$ of said arcuate bottom surface is about 10 mm.

6. A support arm for supporting a surgical light head according to claim 2, wherein a length to with ratio of said cross-section is 68%.

7. A support arm for supporting a surgical light head according to claim 1, wherein said support arm is formed of aluminum.

8. A support arm for supporting a surgical device in an operating room, said support arm comprised of:
- an elongated, tubular extrusion having an inverted, generally tear-drop shaped outer surface that has an airfoil shape, said airfoil shape being symmetrical about an axis extending from a leading end of said airfoil to a trailing end of said airfoil shape, said trailing edge of said airfoil shape having a round contour.

9. A support arm for supporting a surgical device according to claim 8, wherein said outer surface has a shape of a NACA airfoil, wherein said airfoil is symmetrical about a central axis.

10. A support arm for supporting a surgical device according to claim 9, wherein said outer surface has a shape of a NACA 0040 airfoil.

11. A support arm for supporting a surgical device according to claim 8, wherein said outer surface has a maximum thickness to length of between 35% and 50%.

12. A support arm for supporting a surgical device according to claim 8, wherein said outer surface has a maximum thickness to length of 40%.

13. A support arm for supporting a surgical device according to claim 8, wherein said support arm is formed of aluminum.

* * * * *